United States Patent [19]

Peel

[11] 3,975,956
[45] Aug. 24, 1976

[54] SUPPORT HOSIERY TESTING APPARATUS AND METHOD

[75] Inventor: Robert Peel, Winston-Salem, N.C.

[73] Assignee: National Association of Hosiery Manufacturers, Inc., Charlotte, N.C.

[22] Filed: June 23, 1975

[21] Appl. No.: 589,012

[52] U.S. Cl. .................................. 73/159; 33/2 A; 33/137 L
[51] Int. Cl.² ..................... G01L 5/04; G01B 3/02
[58] Field of Search ................. 73/88 R, 95, 159; 33/2 A, 137 L; 66/178 A; 223/77

[56] References Cited
UNITED STATES PATENTS

| | | | |
|---|---|---|---|
| 101,411 | 4/1870 | Bache | 33/137 L |
| 2,189,650 | 2/1940 | Ischinger | 223/77 |
| 2,675,703 | 4/1954 | Hemmerich et al. | 73/159 |
| 3,099,152 | 7/1963 | Krueger | 73/95 |
| 3,457,649 | 7/1969 | Rodgers | 33/137 L |

Primary Examiner—Donald E. Watkins
Assistant Examiner—John S. Appleman
Attorney, Agent, or Firm—Bell, Seltzer, Park & Gibson

[57] ABSTRACT

The stretch and/or compressive forces of hosiery articles are measured by the present apparatus which includes an elongate substantially flat form onto which the hosiery article is drawn for testing. Plungers are supported for sliding movement in the form and the force required to move the plungers and the hosiery fabric outwardly beyond one edge of the form is indicated by the testing apparatus. A signal light is provided for indicating when the plunger and the hosiery fabric have been moved outwardly a predetermined distance from the form. An elastic tape is provided for marking selected points along the length of the hosiery to insure proper positioning of the hosiery on the form.

6 Claims, 3 Drawing Figures

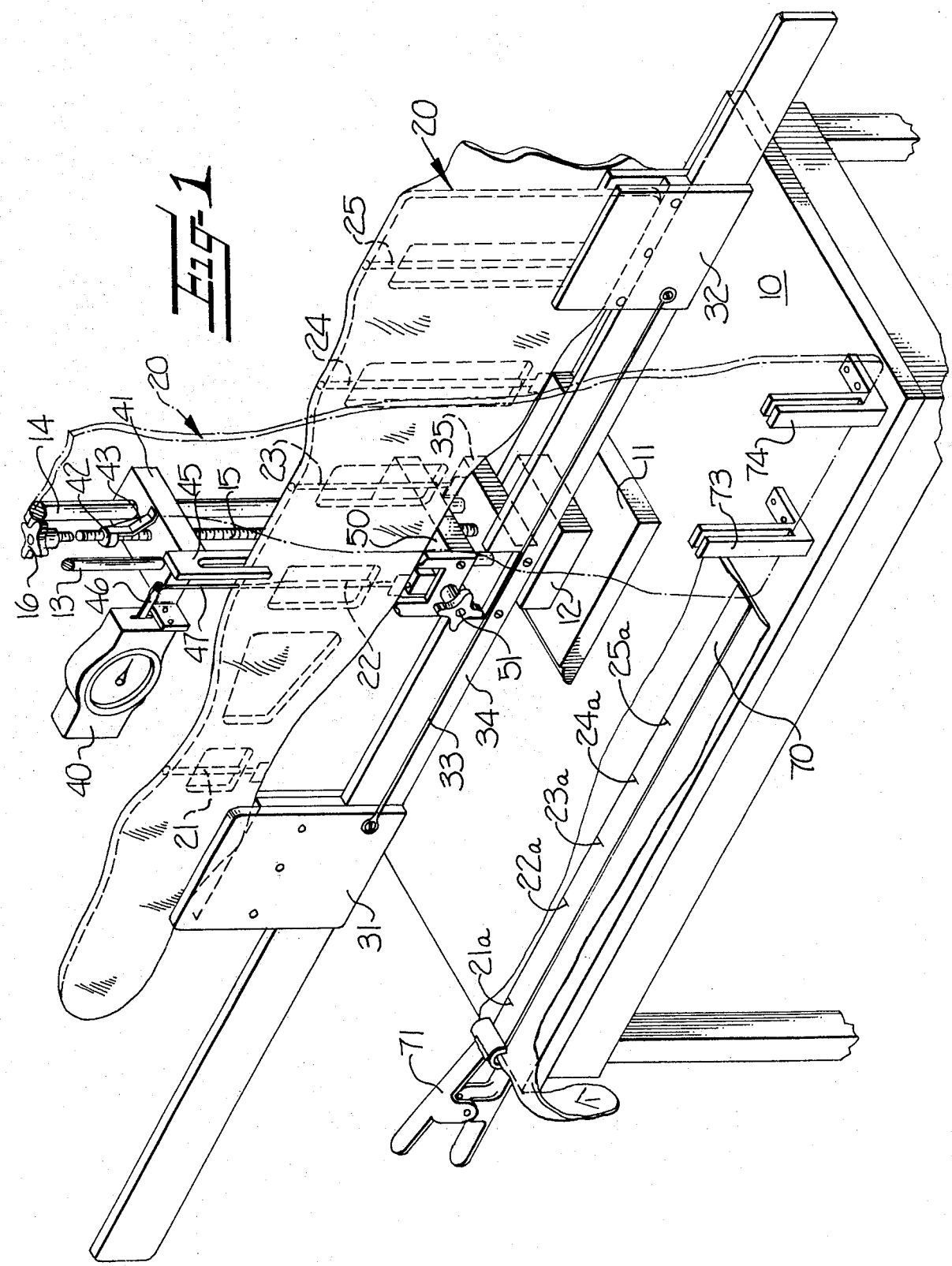

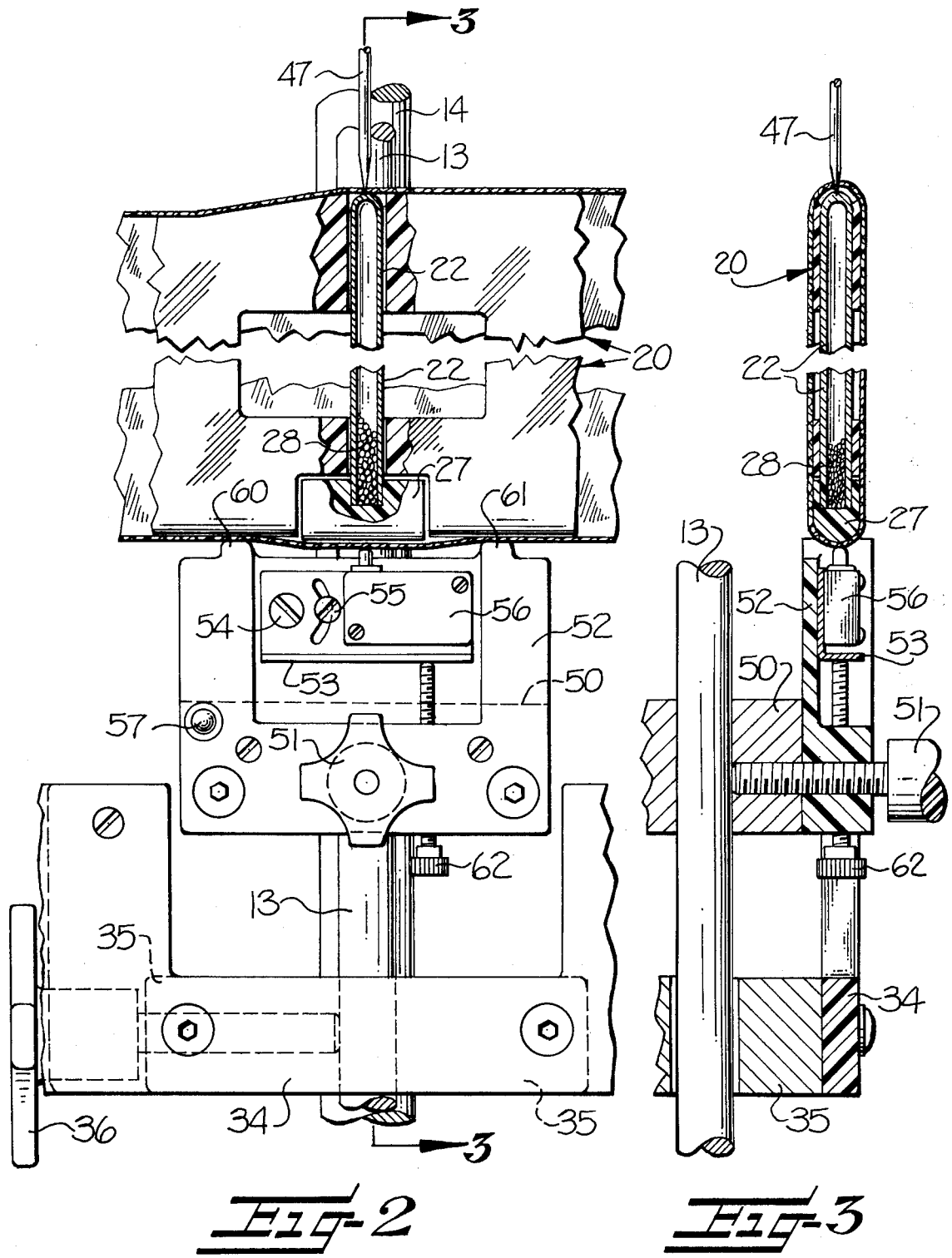

SUPPORT HOSIERY TESTING APPARATUS AND METHOD

This invention relates generally to an apparatus and method for testing the stretch and/or compressive forces of garments and more particularly to an apparatus and method for measuring and comparing the relative compressive forces applied on various portions of the leg by a hosiery article, such as support stockings, panty hose and the like.

Several different types of testing devices have been proposed for measuring the stretch and/or compressive force of hosiery articles. These devices include the use of a mercury manometer device, of the type normally used for measuring blood pressure. Such a device is illustrated in U.S. Pat. No. Re. 25,046. This device includes a rubber bladder which is inflated to a predetermined degree before it is placed in a particular location between the stocking and the leg. The difference between the pressure reading of the inflated bladder before it is placed between the stocking and leg of the wearer and the pressure reading after it is positioned between the stocking and the leg provides an indication of the amount of compressive force applied on the bladder by that particular portion of the stocking. However, the bulge created in the stocking fabric by the inflated bladder does not provide an accurate indication of the force of the stocking against the leg and in order to measure the forces at various portions of the stocking it is necessary to move the bladder to different locations and take a separate reading. The accuracy of this type of device is dependent upon the skill and accuracy of the tester in positioning the bladder and reading the results therefrom.

U.S. Pat. No. 2,675,703 illustrates a hosiery testing device which includes a leg form with rigid strip elements located at certain points along the form. These strip elements are adapted to be moved outwardly against the stocking fabric and weights are employed to apply a circumferential stress to the area of the stocking covering the strip elements. While this device gives some indication of the amount of compressive force which the hosiery article applies against the form, it does not provide a high degree of accuracy. Various other types of devices have also been employed to measure the stretch and/or compressive force characteristics of hosiery articles, however, none of these devices have been widely accepted or employed as a standard in the industry for measuring these characteristics in hosiery articles.

With the foregoing in mind, it is an object of the present invention to provide an apparatus and method for testing the stretch and/or compressive characteristics of hosiery which can be easily utilized to carry out highly reliable and accurate tests, does not destroy the hosiery being tested, can be purchased at a reasonable cost and can be used with very little training for quality control purposes in day to day production.

In accordance with the present invention, the apparatus basically includes two components. The hosiery testing apparatus which includes a plurality of different sized hosiery forms on which the hosiery article is to be placed, and an elastic marking tape for each form which is used to mark the hosiery prior to its being placed on the form to insure accurate positioning of successive hosiery articles on the forms for testing purposes.

The testing apparatus includes a plurality of elongate substantially flat forms of different sizes and having opposite sides suitably contoured so that the hosiery article drawn thereon for testing assumes substantially the same stretched condition the hosiery article would occupy on the leg of the wearer. Plungers are supported for sliding movement in each form and extend from one side of the elongate form to the other. The plungers are spaced at predetermined locations along the form where the hosiery article is to be tested. The hosiery form with the hosiery article positioned thereon is adapted to be supported in carriage members for maintaining the form in a horizontal position and the carriage members may be moved up and down in a vertical direction. A force measuring gauge is supported for vertical movement above the hosiery form and is provided with a needle to successively engage the upper end of each of the plungers and to apply force thereto to move the lower end of the plunger and the portion of the hosiery article covering the lower end of the plunger outwardly beyond the opposite side edge of the form. Signal means is positioned opposite the selected plunger for indicating when the plunger and the hosiery fabric engaged thereby have been moved outwardly of the form a predetermined distance so that the force required to move the plunger and the hosiery fabric outwardly from the hosiery form will be indicated on the force measuring gauge.

The marking device includes an elastic marking tape having spaced indicia indicating the spaced location along the length of the hosiery article to be tested. The elastic marking tape is fixed at one end in a predetermined position adjacent one end portion of the hosiery article when in relaxed condition and the marking tape is stretched along the hosiery article to a predetermined position adjacent the other end of the hosiery article with the spaced indicia corresponding to the spaced locations of the hosiery article to be tested. The hosiery article is then marked with chalk or the like to indicate the position the marked location of hosiery article should assume when the hosiery article is properly positioned on the form for testing.

The apparatus of the present invention is particularly adapted for use in repeated testing operation and insures that exactly the same conditions exist during repeated tests. Since successive tests are carried out under exactly the same conditions, accurate comparisons may be made of the various hosiery articles which are being tested.

Other objects and advantages will appear as the description proceeds when taken in connection with the accompanying drawings, in which FIG. 1 is an isometric view of the testing apparatus and illustrating one hosiery article in position to be marked by use of the elastic marking tape, prior to being placed on the hosiery form, and another hosiery article on the hosiery form and positioned for testing;

FIG. 2 is an enlarged fragmentary front elevational view of the central portion of FIG. 1, with portions being shown in cross-section; and FIG. 3 is a vertical sectional view taken substantially along the line 3—3 in FIG. 2.

The testing apparatus (FIG. 1) is mounted on a work table 10 and includes a pair of support blocks 11, 12 supporting the lower ends of vertical guide shafts 13, 14 and a threaded shaft 15 having a hand wheel 16 fixed to its upper end. A plurality of different size elongate substantially flat hosiery forms, broadly indicated at 20, are provided to test various sizes and types of hosiery articles. For example, it is proposed that twelve different size forms be provided for use in testing different sizes of support stockings. It is preferred that the form 20 be relatively thin, on the order of about one-half inch thick and that the central portion have spaced cut-outs therein to reduce the weight thereof. The form 20 may be formed of plastic or other suitable material.

Force applying means is spaced at selected locations along the form 20 for moving corresponding spaced regions or areas of the hosiery article outwardly of the form. The force applying means is illustrated as spaced plungers 21-25 which are supported for sliding movement and extend from one side of the elongate form 20 to the other. The plungers 21-25 are identical and are spaced to engage and move outwardly areas of the hosiery article at the respective ankle, calf, knee, mid-thigh and maximum thigh position. Since each of the plungers 21-25 is identical, except for variations in length, only the plunger 22, illustrated in FIGS. 2 and 3, will be described in detail. The plunger 22 includes an elongate hollow shaft portion, preferably having a hardened upper closed end portion, and a lower foot portion 27 which has an outer surface conforming to the curved lower edge of the form 20 and positioned in a cut out formed in the lower edge of the form. The foot portion 27 is preferably one inch wide and is covered by the hosiery fabric when the hosiery article is placed on the form 20. Weights, in the form of lead shot 28, are provided in the hollow shaft of the plunger 22 and the amount of weight in the various plungers 21-25 is varied so that the total weight of each plunger is the same.

With the hosiery article positioned on the form, the form 20 is supported in substantially a horizontal position in a pair of form carriers 31, 32 which are connected together by a tie wire 33 and supported for sliding movement along a horizontal support bar 34. The medial portion of the support bar 34 is fixed on the forward end of a support block 35 which is supported for vertical adjustment on the guide shafts 13, 14 by means of an adjustable hand wheel 36 (FIG. 2).

Means for applying downward force to the upper ends of the plungers 21-25 is positioned adjacent the upper side of the form and includes a force measuring gauge 40 which is fixed to a support block 41 supported for sliding movement on the guide shafts 13, 14. The block 41 is supported for vertical movement on the threaded shaft 15 by means of a slotted nut 42 (FIG. 1) which is fixed on the upper end of a leaf spring 43, the lower end of which is fixed on the upper surface of the support block 41. A vertically slotted form aligning plate 45 is fixed on the front portion of the support block 41 and the bifurcated lower legs thereof are adapted to extend downwardly on opposite sides of the form 20 to maintain the form 20 in a vertical position in the form carriers 31, 32. An operating arm 46 extends outwardly from the force measuring gauge 40 and has the upper end of a pointed force applying arm, in the form of a needle 47, pivotally connected thereto. The lower end of the needle 47 is sufficiently sharp so that it will pass through the fabric of the hosiery article covering the upper end of the plunger 22 and directly engage the hardened upper end of the plunger (FIGS. 2 and 3).

Means is provided adjacent the lower edge of the form 20 for indicating when the foot 27 of the plunger 22 and the hosiery fabric engaged thereby is moved outwardly from the form a predetermined distance. Then, the force required to move the plunger and the hosiery fabric outwardly the predetermined distance can be read directly on the force measuring gauge 40. The indicating means includes a support block 50 which is supported for vertical sliding adjustment on the vertical shafts 13, 14 and maintained in adjusted position by means of a threaded hand wheel 51.

A switch support block 52 is fixed to the front surface of the support block 50 and a switch support plate 53 is pivotally supported at one end on a pivot screw 54 and maintained in adjusted position by a lock screw 55 which penetrates in an arcuate slot in the switch support plate 53. A low operating pressure microswitch 56 is supported on the plate 53 and has an upwardly extending operating plunger aligned with the center of the foot portion 27 of the plunger 22 for indicating when the force applied to the upper end of the plunger 22 has moved the selected area of the hosiery article outwardly below the form 20 the predetermined distance. An indicator light 57 is supported in the switch support block 52 and is electrically connected to the switch 56 so that the light will turn on when the hosiery fabric moves down to close the switch 56.

The upper portion of the switch block 52 is provided with upstanding support ears 60, 61 which are equally spaced on opposite sides of the operating plunger of the microswitch 56. The ears 60, 61 are adapted to be raised upwardly to engage the lower edge of the hosiery form 20 and the hosiery fabric when the hosiery is to be tested, in a manner to be presently described. A vernier screw 62 is threadably supported in the switch block 52 and the lower end thereof is adapted to engage the lower surface of the switch support plate 53 for purposes of adjusting the position of the microswitch 56, in a manner to be presently described.

An elastic marking tape 70 (FIG. 1) comprises an important part of the present testing apparatus and may be formed of knitted or woven stretchable yarn. The tape 70 is provided with spaced indicia, indicated at 21a through 25a which correspond to the spaced regions or areas of the hosiery article to be tested. An elastic marking tape 70 is provided for each size of hosiery form 20 and the proper tape is used to prepare the hosiery to be tested so that it may be positioned on the form 20 in the proper position for testing selected areas of the stocking. To mark and prepare the hosiery article for testing, the lower edge of the heel portion of the hosiery article is aligned with one end of the elastic marking tape 70 and they are both held in alignment with the edge of the table 10 by means of a spring clip or clamp 71. The hosiery article is then straightened out in relaxed condition on the table 10 and the elastic marking tape 70 is stretched along the length of the hosiery article until the free end thereof is aligned with the upper end of the hosiery article, in the case of a stocking, or in the crotch area, in the case of a panty hose article.

The relaxed stocking is then marked transversely with a marking chalk at each of the corresponding indicia 21a through 25a on the elastic marking tape 70 to provide reference points on the stocking to be tested, which reference points will be aligned with the corresponding plungers 21-25 when the stocking is placed on the hosiery form. Spaced support brackets 73, 74 are provided on the table 10 for supporting the hosiery form 20 in a vertical position while the stocking is drawn down on the form and the chalk marks are aligned with the corresponding plungers in the areas of the stocking to be tested.

METHOD OF OPERATION

When the hosiery article is properly aligned on the form 20, with the chalk marks aligned with the plungers 21–25, the toe end portion of the form 20 is placed in the form carrier 31 and the upper portion is placed in the form carrier 32. The support block 50 and support 34 are then in a lowered position while the block 41 and the gauge 40 are in a raised position. The carrier blocks 31, 32 may then be moved along the support bar 34 to properly align any one of the plungers 21–25 with the area where the first testing operation is to take place. Normally, the test will be conducted from adjacent one end of the form to the other and it may be desirable to first test the ankle area which is covering the plunger 21. However, the testing at each area is identical and the testing of the calf area, covered by the plunger 22, will be described in detail.

With the carrier blocks 31, 32 positioned as shown in FIG. 1, so that the operating plunger of the microswitch 56 is aligned beneath the center of the foot 27 of the plunger 22, the block 50 is raised until the upstanding ears 60, 61 engage the lower edge of the form and the hosiery article thereon, as shown in FIG. 2, and the hand wheel 51 is tightened to hold the block 50 in this position. The block 41 is then lowered by moving the slotted nut 42 away from the threaded shaft 15 until the lower end of the needle 47 is just above the form 20 and the legs of the plate 45 straddle the upper portion of the form. The screws 54, 55 are then loosened and the microswitch 56 and bracket 53 are lowered by lowering away from the hosiery fabric by turning the vernier screw 62. The upper end of the plunger of the microswitch 56 is then adjusted a predetermined distance below the hosiery article on the inspection form and below the foot 27 on the plunger 22.

It is preferred that a thickness gauge be utilized to set the operating plunger of the microswitch 56 a predetermined distance below the lower edge of the form. While this clearance may be varied, it has been found that a clearance of 0.025 inch is sufficient. The screws 54, 55 are then tightened after the proper clearance has been obtained. After the microswitch 56 is set, the block 41 is further lowered so that the lower end of the needle 47 penetrates the fabric and is moved into engagement with the upper hardened end of the plunger 22 by rotation of the hand wheel 16 to rotate the threaded shaft 15.

With continued rotation of the hand wheel to lower the gauge 40, a force is applied to the upper end of the plunger 22 to move the lower foot end 27 outwardly beyond the lower side edge of the form 20 and to thereby move the hosiery fabric engaged thereby outwardly a predetermined distance, until the operating plunger of the microswitch 56 is sufficiently depressed to cause the indicator or signal light 57 to come on. When the light 57 turns on, the amount of force required to move the plunger 22 and the hosiery fabric outwardly below the lower edge of the form 20 can be read directly from the force measuring gauge 40 and recorded.

While some indication of the amount of stretch and/or compressive force of the hosiery article on the hosiery form would be obtained by merely reading the force required to move the plungers outwardly at each of the spaced locations, it is preferred that the pressure or compressive force be calculated with these force readings, in a manner to be presently described. It is also preferred that several readings be taken at each location, for example three readings, and that these readings be averaged and then the pressure or compressive force is calculated to determine the pressure or compressive force in a one inch circular band of the stocking which is engaged by the foot 27 of the plunger 22.

After the average force measurement has been determined by taking three readings and averaging the three readings, it is used to calculate the compressive force or pressure of the housing by using a mathematical formula. The formula used is $P = 2T/dl$ where P equals pressure or compressive force, 2T equals the sum of the tension in both sides of the fabric on the form (the average of the readings obtained on the gauge 40), $d$ equals the diameter of girth of the hosiery fabric at that location, and $l$ equals the width of the diameter or girth. Since $d \times l$ is equal to the area of the cross-section and the width is always the same, the $l$ can be eliminated and the formula then becomes 2T divided by the diameter or girth. It will be understood that the girth of the form at the various plungers 21–25 will vary and in a medium size form of the type illustrated in the drawings, the various girth dimensions are as follows:

| | |
|---|---|
| Ankle Girth, at Plunger 21 | 9.30" |
| Calf Girth, at Plunger 22 | 13.42" |
| Knee Girth, at Plunger 23 | 13.92" |
| Mid-Thigh Girth, at Plunger 24 | 19.51" |
| Maximum Thigh Girth, at Plunger 25 | 22.17" |

If the force readings of the gauge 40 are taken in ounces or pounds, the diameter in inches will be used and the resulting compressive force or pressure will be determined and expressed in ounces or pounds per square inch. However, it is to be understood that the measurements to be used in the tests may be converted so that the results will be in any system desired.

In the manufacture of ladies' support stockings, it has been found desirable to knit them in such a manner as to provide a gradually decreasing compressive force or pressure from the ankle upwardly to the thigh. The present testing apparatus and method provides an economical and efficient means by which it can be determined if the hosiery is properly manufactured to produce this type of gradual and upwardly reducing pressure when worn on the leg.

There are many variable factors which determine the size of hosiery produced on a circular hosiery knitting machine, such as yarn tension, stitch cam position, needle alignment, operation of the sinkers, etc. These variable factors make it almost impossible to consistently produce the same size hosiery articles which are the same length in the relaxed condition. Therefore, the elastic measuring and marking tape 70, for each size of form 20, is shorter between the first indicia and the last indicia than a relaxed hosiery article of a given size is ever likely to be. Thus, the elastic measuring and marking tape 70 must be stretched to some degree in order to properly align the indicia with the corresponding areas of the hosiery article to be marked for positioning on the hosiery form.

In the drawings and specification there has been set forth a preferred embodiment of the invention, and although specific terms are employed, they are used in That which is claimed is:

1. An apparatus for the non-destructive testing of the compressive force of hosiery articles comprising
   a. an elongate form onto which the hosiery article is drawn for testing,
   b. means spaced along said form for moving corresponding spaced regions of the hosiery article outwardly of said form a predetermined distance,
   c. means for indicating when the spaced regions of the hosiery article have been moved outwardly said predetermined distance,
   d. means operatively associated with said form for indicating the amount of force required to move said spaced regions of the hosiery article outwardly of said form said predetermined distance, and
   e. an elastic marking tape including spaced indicia indicating the spaced regions of the hosiery article to be tested, said elastic marking tape being adapted to be fixed at one end in a predetermined position adjacent one end of the hosiery article when in relaxed condition and prior to being drawn on said form, said elastic marking tape also being adapted to be stretched along the length of the hosiery article to a predetermined position adjacent the other end of the hosiery article with said spaced indicia corresponding to said spaced regions of the hosiery article to be tested so that the hosiery article may be marked to indicate when the hosiery article is properly positioned on said form for testing.

2. An apparatus for the non-destructive testing of the compressive force of hosiery articles comprising
   a. an elongate substantially flat form having opposite sides suitably contoured so that the hosiery article drawn thereon for testing assumes substantially the same stretched condition the hosiery article occupies on the leg of the wearer,
   b. plungers supported for sliding movement and extending from one side of said elongate form to the other and being spaced along the form,
   c. force applying and measuring means positioned adjacent one side and exteriorly of said form for penetrating the hosiery article and selectively engaging one end of said plungers and applying force thereto to move the other end of said plunger and the portion of the hosiery article covering said other end of said plunger outwardly beyond the opposite side edge of said elongate form, and
   d. means positioned opposite said selected plunger for indicating when said plunger and the hosiery fabric engaged thereby is moved outwardly of the form a predetermined distance so that the force required to move the plunger and the hosiery fabric outwardly from the hosiery form the predetermined distance can be determined.

3. In an apparatus according to claim 2 wherein said plungers (b) vary in length, depending upon their position in the form, and including means for varying the weight of said plungers so that they are of the same weight, regardless of their length.

4. An apparatus according to claim 2 wherein said means (c) comprises a force measuring gauge and a sharpened needle connected thereto, said sharpened needle being adapted to penetrate the fabric covering said one end of said plunger to move the same without moving the fabric covering said one end of said plunger.

5. An apparatus according to claim 2 wherein said means (d) comprises a microswitch including an operating plunger positioned a predetermined distance away from said other end of said plunger, and an indicator light for indicating when said plunger has been moved outwardly a sufficient distance to close said microswitch and signal the movement of the said plunger said predetermined distance.

6. A method of testing the compressive force of hosiery articles without destroying the hosiery articles comprising the steps of
   a. fixing one end of an elastic marking tape adjacent one end of a relaxed and flattened hosiery article,
   b. stretching the other end of the elastic tape along the said relaxed hosiery article and to a particular point adjacent the other end of the hosiery article,
   c. marking spaced points along the length of the hosiery articles to correspond with indicia on the elastic marking tape,
   d. drawing the hosiery article onto an elongate form having plungers supported for transverse sliding movement at spaced locations along the form,
   e. aligning the marked points on the hosiery with the plungers in said form,
   f. penetrating the hosiery article and applying pressure successively to one end of the plungers along the hosiery form to force the portion of the hosiery article covering the other end of the plungers outwardly away from the form a predetermined distance, and
   g. determining the amount of force required to move the hosiery fabric outwardly from the form said predetermined distance.

* * * * *